US006767893B2

(12) United States Patent
Ammons et al.

(10) Patent No.: US 6,767,893 B2
(45) Date of Patent: Jul. 27, 2004

(54) METHOD OF TREATING CONDITIONS ASSOCIATED WITH INTESTINAL ISCHEMIA/REPERFUSION

(75) Inventors: William Steve Ammons, Pinole, CA (US); Károly M. Mészáros, San Ramon, CA (US)

(73) Assignee: Xoma Corporation, Berkeley, CA (US)

( * ) Notice: Subject to any disclaimer, the term of this patent is extended or adjusted under 35 U.S.C. 154(b) by 0 days.

(21) Appl. No.: 09/416,828

(22) Filed: Oct. 12, 1999

(65) Prior Publication Data

US 2003/0171265 A1 Sep. 11, 2003

Related U.S. Application Data

(63) Continuation of application No. 08/756,164, filed on Nov. 25, 1996, now Pat. No. 6,017,851, which is a continuation of application No. 08/232,527, filed on Apr. 22, 1994, now Pat. No. 5,578,568.

(51) Int. Cl.$^7$ .......................... A61K 38/17; C07K 14/46

(52) U.S. Cl. ......................................... 514/12; 530/350

(58) Field of Search ............................. 514/12; 530/350

(56) References Cited

U.S. PATENT DOCUMENTS

| | | | | |
|---|---|---|---|---|
| 5,089,274 A | | 2/1992 | Marra et al. ................. | 424/534 |
| 5,153,178 A | | 10/1992 | Maroko ........................ | 514/26 |
| 5,171,739 A | | 12/1992 | Scott ............................ | 514/12 |
| 5,198,541 A | | 3/1993 | Elsbach et al. ............. | 435/69.1 |
| 5,234,912 A | | 8/1993 | Marra et al. .................. | 514/21 |
| 5,308,834 A | | 5/1994 | Scott et al. .................... | 514/12 |
| 5,334,584 A | | 8/1994 | Scott et al. .................... | 514/12 |
| 5,420,019 A | * | 5/1995 | Theofan et al. ............. | 435/69.1 |

FOREIGN PATENT DOCUMENTS

| | | |
|---|---|---|
| WO | WO 89/12644 | 12/1989 |
| WO | WO 92/03535 | 3/1992 |
| WO | WO 92/09261 | 6/1992 |
| WO | WO 93/06228 | 4/1993 |
| WO | WO 93/23434 | 11/1993 |
| WO | WO 93/23540 | 11/1993 |

OTHER PUBLICATIONS

Stedman's Medical Dictionary Search [online]. PDR® Electronic Library by Medical Economics Company, Inc. at Montvale, NJ 07645. [retrieved on Feb. 20, 2002]. Retrieved from Internet:<URL:http://www.pdrel.com/pdr/static.htm?path=controlled/searchstedman>.*
Grace PA. Ischaemia–reperfusion injury. Br J Surg. May 1994;81(5):637–47.*
Horton et al. Oxygen radicals, lipid peroxidation, and permeability changes after intestinal ischemia and reperfusion. J Appl Physiol. Apr. 1993;74(4):1515–20.*
Bone R C. Why sepsis trials fail. JAMA, (Aug. 21, 1996) 276 (7) 565–6.*

Bowie et al. Deciphering the message in protein sequences: tolerance to amino acid substitutions. Science, (Mar. 16, 1990) 247 (4948) 1306–10.*
Ngo et al., in The Protein Folding Problem and Tertiary Structure Prediction, Merz and Le Grand (Eds), Aug. 1994, Springer Verlag, pp. 433 and 492–495.*
Ammons, et al., An N–Terminal Fragment Of Bactericidal/Permeability Increasing Protein (rBPI$_{21}$) Reduces Cardiorespiratory Dysfunction Resulting From Intestinal Ischemia/Reperfusion, *Annual Meeting of Professional Scientific Research Scientists, Experimental Biology 94*™, Anaheim, California, Abstracts 1–3391, Part I, Ischemic Injury, 753 (Apr. 24–28, 1994).
Bahrami, et al., "Endotoxemia In Rats Subjected To The Haemorrhage: Effects Of Bactericidal/Permeability Increasing Protein (BPI)", *Abstract Presented At Vienna International Endotoxin Society Meeting* (Aug., 1992).
Bahrami, et al., "Bactericidal/Permeability–Increasing Protein (BPI) Reduces Lipopolysaccride (LPS)–Induced Cytokine Formation And Mortality In Rats," *Circulatory Shock*, Supplement 1, Abstract 12.25P, Vienna, Austria (May 9–13, 1993).
Boermeester, et al., "Peri–operative prophylaxis with bactericidal/permeability–increasing protein (rBPI$_{23}$) prevents early postoperative derangements following partial hepatectomy," *Intensive Care Medicine*, vol. 20, Supplement 1, Abstract 478 (Mar., 1994).
Elsbach, et al., "Separation and Purification of a Potent Bactericidal/Permeability–increasing Protein and a Closely Associated Phospholipase A$_2$ from Rabbit Polymorphonuclear Leukocytes," *The Journal of Biological Chemistry*, vol. 21, 11000–11009 (Nov. 10, 979).
Gathiram, et al., "Changes in Lipopolysaccharide Concentrations in Hepatic Portal and Systematic Arterial Plasma During Intestinal Ischemia in Monkeys," *Circulatory Shock*, vol. 27, 103–109 (1989).
Gazzano–Santoro, et al., "High–Affinity Binding of the Bactericidal/Permeability–Increasing Protein and a Recombinant Amino–Terminal Fragment to the Lipid A Region of Lipopolysaccharide," *Infection and Immunity*, vol. 60, 4754–4761, (Nov., 1992).
Gray, et al., "Cloning of the cDNA of a Human Neutrophil Bactericidal Protein," *The Journal of Biological Chemistry*, vol. 264, No. 16, 9505–9509 (Jun., 1989).
Mainous, et al., "Bacterial Translocation," *Pathophysiology of Shock, Sepsis, and Organ Failure*, Springer–Verlag, 265–278 (1993).

(List continued on next page.)

*Primary Examiner*—David S. Romeo
(74) *Attorney, Agent, or Firm*—Marshall, Gerstein & Borun LLP

(57) ABSTRACT

The present invention provides methods of treating adverse physiological effects associated with intestinal ischemia/reperfusion by administering to a subject suffering from the effects of intestinal ischemia/reperfusion an effective amount of a BPI protein product.

8 Claims, 4 Drawing Sheets

OTHER PUBLICATIONS

Ooi, et al., "Endotoxin–neutralizing Properties of the 25 kD N–Terminal Fragment and a Newly Isolated 30 kD C–Terminal Fragment of the 55–60 kD Bactericidal/Permeability–increasing Protein of Human Neutrophils," *J. Exp. Med.*, vol. 174, 649–655 (Sep., 1991).

Weiss, et al., "Cellular and Subcellular Localization of the Bactericidal/Permeability–Increasing Protein of Neutrophils," *Blood*, vol. 69, No. 2, 652–659 (Feb., 1987).

Yao, et al., "Effects Of Bactericidal/Permeability Increasing Protein (BPI) Against Haemorrage–Induced Endotoxemia And Mortality In Rats," *Intensive Care Medicine*, vol. 20, Supplement 1, Abstract 479 (Mar., 1994).

Bone, *Ann. Internal Med*, 115(6): 457–469 (1991).

Glauser et al., *Lancet*, 338: 732–736 (1991).

Kilbourn et al., *J. National Cancer Institute*, 84(11): 827–831 (1992).

Natanson et al., *Ann. Internal Med.*, 120(9): 771–783 (1994).

*The Economist*, "Panic in the Petri Dish," pp. 61–62 (Jul. 23, 1994).

Cross et al., Infect. Immun., 61: 2741–2747 (1993).

Petros et al., *Lancet*, 338: 1557–1558 (1991).

Bahrami et al., "Endotoxemia in Rats Subjected to the Haemorrhage: Effects of Bactericidal/Permeability Increasing Protein (BPI)," Intl. Conf. on Endotoxins, Amsterdam, Aug. 17–20, 1993.

Little et al., "Functional Domains of Recombinant Bactericidal/Permeability Increasing Protein ($rBPI_{23}$)," *J. Biol. Chem.*, 269:1865–1872 (1994).

Von der Mohlen et al., "Effect of $rBPI_{23}$ on Endotoxin–Induced Cytokine Release and Leukocyte Changes in Human Volunteers," Clinical Research Meeting, Apr. 29–May 2, 1994.

Von der Mohlen et al., "Inhibition of Endotoxin–Induced Cytokine Release and Neutrophil Activation in Humans by Use of Recombinant Bactericidal/Permeability–Increasing Protein," *J. Infect. Dis.*, 172:144–51 (1995).

Von der Mohlen et al., "Inhibition of Endotoxin–Induced Activation of the Coagulation and Fibrinolytic Pathways Using a Recombinant Endotoxin–Binding Protein ($rBPI_{23}$)," *Blood*, 85:3437–3443 (1995).

Novotny et al. "Evidence for lack of importance of oxygen free radicals in *Eschrichia coli* endotoxemia in dogs" *Am. J. Physiol.* 254 (5 Pt 2): H954–62, (1988) Abstract only provided.

Velkov, "Changes in rabbit cardiac function during fulminant endotoxin shock." *Acta Physiol Pharmacol Bulg.* 20 (1):19–24 (1994) Abstract only provided.

Bone "Gram–negative sepsis". Background, clinical features, and intervention. *Chest*, 100 (3) 802–8 (1991), Abstract only provided.

Caty et al, "Evidence for tumor necrosis factor–induced pulmonary microvascular injury after intestinal ischemia–reperfusion injury" *Annals of Surgery* 212 (6):694–700 (1990).

\* cited by examiner

FIGURE 3
rBPI$_{21}$ Reduces Hypotension Resulting from Intestinal Ischemia/Reperfusion Injury
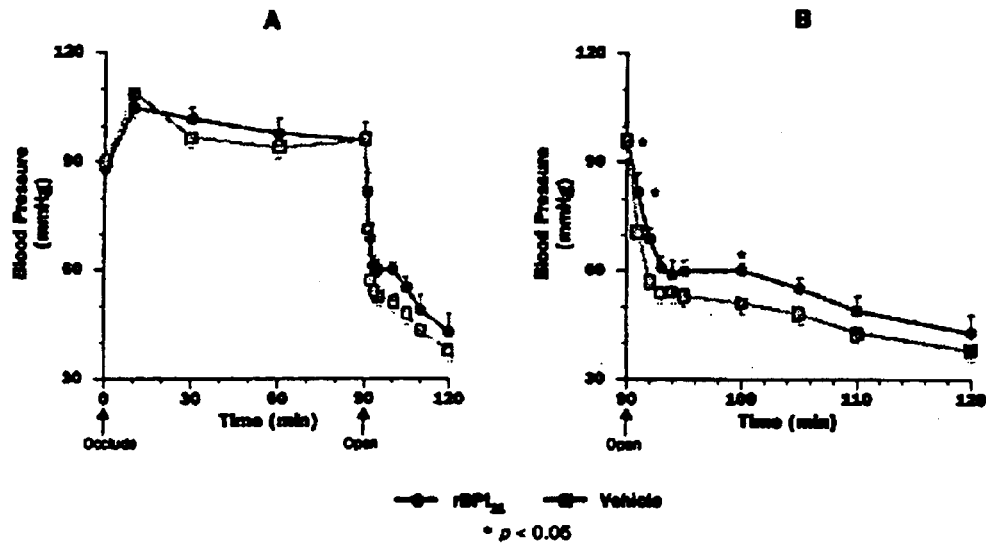
FIG. 3A            FIG. 3B
FIGURE 4
rBPI$_{21}$ Prevents Bradycardia Resulting from Intestinal Ischemia/Reperfusion Injury
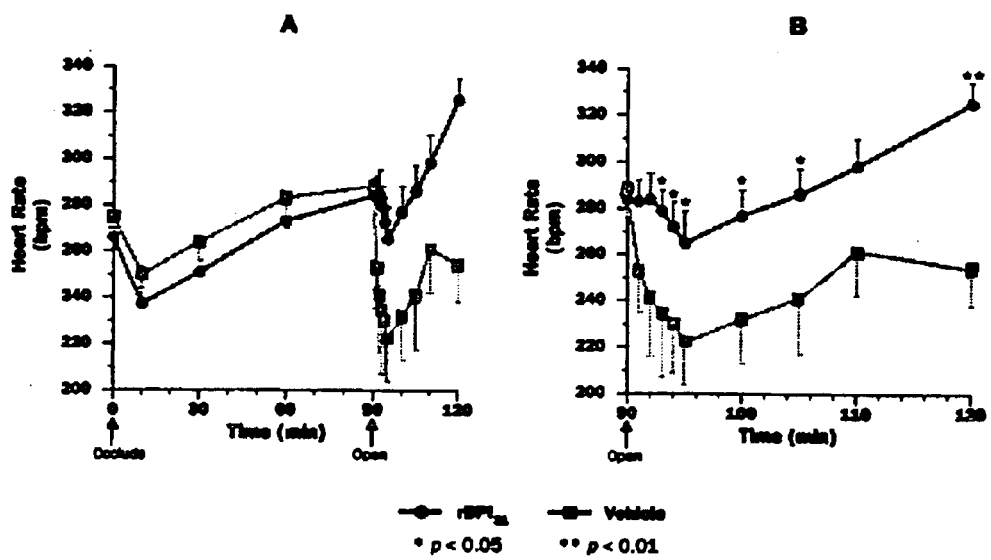
FIG. 4A            FIG. 4B FIGURE 5
rBPI$_{21}$ Reduces Respiratory Depression Resulting from Intestinal Reperfusion
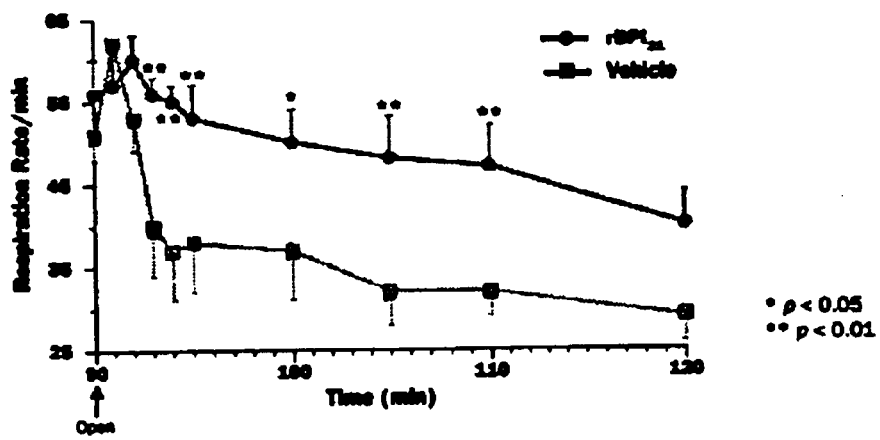
FIG. 5
FIGURE 6
rBPI$_{21}$ Reduces Arrythmias in Intestinal Ischemia/Reperfusion Injury
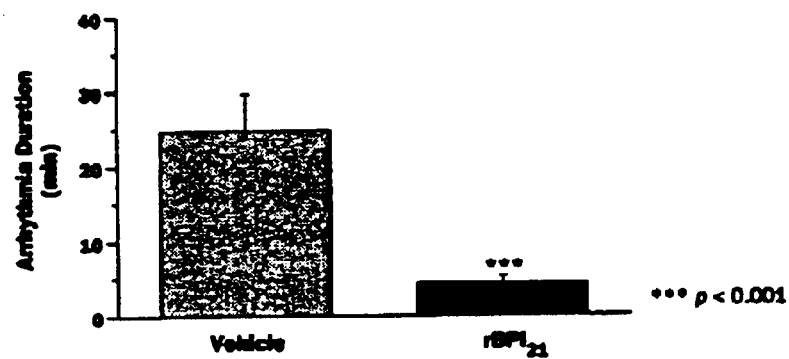
FIG. 6

FIGURE 7
rBPI$_{21}$ Treatment Increases Survival Time
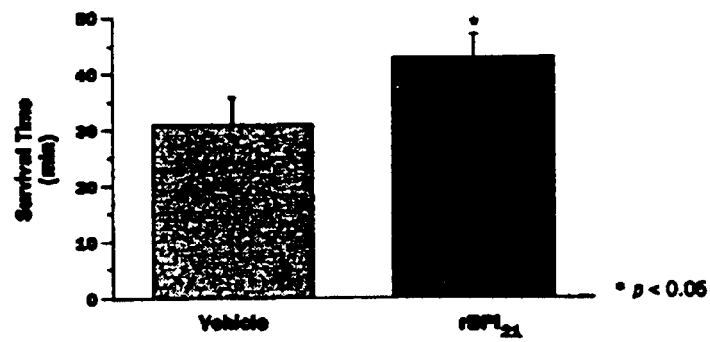
FIG. 7
FIGURE 8
rBPI$_{21}$ Reduces Translocation of Bacteria Resulting from Intestinal Ischemia/Reperfusion
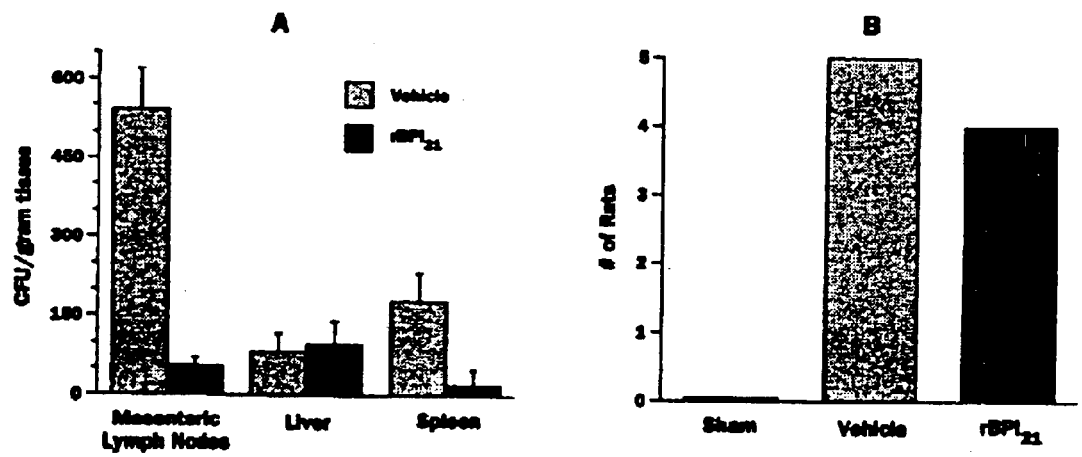
FIG. 8A          FIG. 8B

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1813 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 31..1491

(ix) FEATURE:
      (A) NAME/KEY: mat_peptide
      (B) LOCATION: 124..1491

(ix) FEATURE:
      (A) NAME/KEY: misc_feature
      (D) OTHER INFORMATION: "rBPI"

(xi) SEQUENCE DESCRIPTION: SEQ ID NO:1:

```
CAGGCCTTGA GGTTTTGGCA GCTCTGGAGG ATG AGA GAG AAC ATG GCC AGG GGC      54
                                Met Arg Glu Asn Met Ala Arg Gly
                                -31 -30                      -25

CCT TGC AAC GCG CCG AGA TGG GTG TCC CTG ATG GTG CTC GTC GCC ATA      102
Pro Cys Asn Ala Pro Arg Trp Val Ser Leu Met Val Leu Val Ala Ile
            -20             -15                 -10

GGC ACC GCC GTG ACA GCG GCC GTC AAC CCT GGC GTC GTG GTC AGG ATC      150
Gly Thr Ala Val Thr Ala Ala Val Asn Pro Gly Val Val Val Arg Ile
        -5                   1               5

TCC CAG AAG GGC CTG GAC TAC GCC AGC CAG CAG GGG ACG GCC GCT CTG      198
Ser Gln Lys Gly Leu Asp Tyr Ala Ser Gln Gln Gly Thr Ala Ala Leu
 10              15                  20                  25

CAG AAG GAG CTG AAG AGG ATC AAG ATT CCT GAC TAC TCA GAC AGC TTT      246
Gln Lys Glu Leu Lys Arg Ile Lys Ile Pro Asp Tyr Ser Asp Ser Phe
                30                  35                  40

AAG ATC AAG CAT CTT GGG AAG GGG CAT TAT AGC TTC TAC AGC ATG GAC      294
Lys Ile Lys His Leu Gly Lys Gly His Tyr Ser Phe Tyr Ser Met Asp
            45                  50                  55

ATC CGT GAA TTC CAG CTT CCC AGT TCC CAG ATA AGC ATG GTG CCC AAT      342
Ile Arg Glu Phe Gln Leu Pro Ser Ser Gln Ile Ser Met Val Pro Asn
        60                  65                  70

GTG GGC CTT AAG TTC TCC ATC AGC AAC GCC AAT ATC AAG ATC AGC GGG      390
Val Gly Leu Lys Phe Ser Ile Ser Asn Ala Asn Ile Lys Ile Ser Gly
    75                  80                  85

AAA TGG AAG GCA CAA AAG AGA TTC TTA AAA ATG AGC GGC AAT TTT GAC      438
Lys Trp Lys Ala Gln Lys Arg Phe Leu Lys Met Ser Gly Asn Phe Asp
 90                  95                 100                 105

CTG AGC ATA GAA GGC ATG TCC ATT TCG GCT GAT CTG AAG CTG GGC AGT      486
Leu Ser Ile Glu Gly Met Ser Ile Ser Ala Asp Leu Lys Leu Gly Ser
                110                 115                 120

AAC CCC ACG TCA GGC AAG CCC ACC ATC ACC TGC TCC AGC TGC AGC AGC      534
Asn Pro Thr Ser Gly Lys Pro Thr Ile Thr Cys Ser Ser Cys Ser Ser
            125                 130                 135

CAC ATC AAC AGT GTC CAC GTG CAC ATC TCA AAG AGC AAA GTC GGG TGG      582
His Ile Asn Ser Val His Val His Ile Ser Lys Ser Lys Val Gly Trp
        140                 145                 150
```

-continued

```
CTG ATC CAA CTC TTC CAC AAA AAA ATT GAG TCT GCG CTT CGA AAC AAG        630
Leu Ile Gln Leu Phe His Lys Lys Ile Glu Ser Ala Leu Arg Asn Lys
    155                 160                 165

ATG AAC AGC CAG GTC TGC GAG AAA GTG ACC AAT TCT GTA TCC TCC AAG        678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT        726
Leu Gln Pro Tyr Phe Gln Thr Leu Pro Val Met Thr Lys Ile Asp Ser
                190                 195                 200

GTG GCT GGA ATC AAC TAT GGT CTG GTG GCA CCT CCA GCA ACC ACG GCT        774
Val Ala Gly Ile Asn Tyr Gly Leu Val Ala Pro Pro Ala Thr Thr Ala
            205                 210                 215

GAG ACC CTG GAT GTA CAG ATG AAG GGG GAG TTT TAC AGT GAG AAC CAC        822
Glu Thr Leu Asp Val Gln Met Lys Gly Glu Phe Tyr Ser Glu Asn His
        220                 225                 230

CAC AAT CCA CCT CCC TTT GCT CCA CCA GTG ATG GAG TTT CCC GCT GCC        870
His Asn Pro Pro Pro Phe Ala Pro Pro Val Met Glu Phe Pro Ala Ala
    235                 240                 245

CAT GAC CGC ATG GTA TAC CTG GGC CTC TCA GAC TAC TTC TTC AAC ACA        918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA        966
Ala Gly Leu Val Tyr Gln Glu Ala Gly Val Leu Lys Met Thr Leu Arg
                270                 275                 280

GAT GAC ATG ATT CCA AAG GAG TCC AAA TTT CGA CTG ACA ACC AAG TTC       1014
Asp Asp Met Ile Pro Lys Glu Ser Lys Phe Arg Leu Thr Thr Lys Phe
            285                 290                 295

TTT GGA ACC TTC CTA CCT GAG GTG GCC AAG AAG TTT CCC AAC ATG AAG       1062
Phe Gly Thr Phe Leu Pro Glu Val Ala Lys Lys Phe Pro Asn Met Lys
        300                 305                 310

ATA CAG ATC CAT GTC TCA GCC TCC ACC CCG CCA CAC CTG TCT GTG CAG       1110
Ile Gln Ile His Val Ser Ala Ser Thr Pro Pro His Leu Ser Val Gln
    315                 320                 325

CCC ACC GGC CTT ACC TTC TAC CCT GCC GTG GAT GTC CAG GCC TTT GCC       1158
Pro Thr Gly Leu Thr Phe Tyr Pro Ala Val Asp Val Gln Ala Phe Ala
330                 335                 340                 345

GTC CTC CCC AAC TCC TCC CTG GCT TCC CTC TTC CTG ATT GGC ATG CAC       1206
Val Leu Pro Asn Ser Ser Leu Ala Ser Leu Phe Leu Ile Gly Met His
                350                 355                 360

ACA ACT GGT TCC ATG GAG GTC AGC GCC GAG TCC AAC AGG CTT GTT GGA       1254
Thr Thr Gly Ser Met Glu Val Ser Ala Glu Ser Asn Arg Leu Val Gly
            365                 370                 375

GAG CTC AAG CTG GAT AGG CTG CTC CTG GAA CTG AAG CAC TCA AAT ATT       1302
Glu Leu Lys Leu Asp Arg Leu Leu Leu Glu Leu Lys His Ser Asn Ile
        380                 385                 390

GGC CCC TTC CCG GTT GAA TTG CTG CAG GAT ATC ATG AAC TAC ATT GTA       1350
Gly Pro Phe Pro Val Glu Leu Leu Gln Asp Ile Met Asn Tyr Ile Val
    395                 400                 405

CCC ATT CTT GTG CTG CCC AGG GTT AAC GAG AAA CTA CAG AAA GGC TTC       1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG       1446
Pro Leu Pro Thr Pro Ala Arg Val Gln Leu Tyr Asn Val Val Leu Gln
                430                 435                 440

CCT CAC CAG AAC TTC CTG CTG TTC GGT GCA GAC GTT GTC TAT AAA           1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC    1551
```

-continued

```
ACCGGCTGCC TTTCCCCAGG GAATCCTCTC CAGATCTTAA CCAAGAGCCC CTTGCAAACT    1611

TCTTCGACTC AGATTCAGAA ATGATCTAAA CACGAGGAAA CATTATTCAT TGGAAAAGTG    1671

CATGGTGTGT ATTTTAGGGA TTATGAGCTT CTTTCAAGGG CTAAGGCTGC AGAGATATTT    1731

CCTCCAGGAA TCGTGTTTCA ATTGTAACCA AGAAATTTCC ATTTGTGCTT CATGAAAAAA    1791

AACTTCTGGT TTTTTTCATG TG                                             1813
```

(2) INFORMATION FOR SEQ ID NO:2:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Glu Asn Met Ala Arg Gly Pro Cys Asn Ala Pro Arg Trp Val
-31 -30                 -25                 -20

Ser Leu Met Val Leu Val Ala Ile Gly Thr Ala Val Thr Ala Ala Val
-15             -10                  -5                        1

Asn Pro Gly Val Val Arg Ile Ser Gln Lys Gly Leu Asp Tyr Ala
              5                  10                  15

Ser Gln Gln Gly Thr Ala Ala Leu Gln Lys Glu Leu Lys Arg Ile Lys
           20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
 50              55                  60                       65

Ser Gln Ile Ser Met Val Pro Asn Val Gly Leu Lys Phe Ser Ile Ser
                70                  75                  80

Asn Ala Asn Ile Lys Ile Ser Gly Lys Trp Lys Ala Gln Lys Arg Phe
             85                  90                  95

Leu Lys Met Ser Gly Asn Phe Asp Leu Ser Ile Glu Gly Met Ser Ile
         100                 105                 110

Ser Ala Asp Leu Lys Leu Gly Ser Asn Pro Thr Ser Gly Lys Pro Thr
     115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
             165                 170                 175

Val Thr Asn Ser Val Ser Ser Lys Leu Gln Pro Tyr Phe Gln Thr Leu
         180                 185                 190

Pro Val Met Thr Lys Ile Asp Ser Val Ala Gly Ile Asn Tyr Gly Leu
     195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
             245                 250                 255

Leu Ser Asp Tyr Phe Phe Asn Thr Ala Gly Leu Val Tyr Gln Glu Ala
         260                 265                 270
```

-continued

```
Gly Val Leu Lys Met Thr Leu Arg Asp Asp Met Ile Pro Lys Glu Ser
    275             280             285

Lys Phe Arg Leu Thr Thr Lys Phe Phe Gly Thr Phe Leu Pro Glu Val
290             295             300             305

Ala Lys Lys Phe Pro Asn Met Lys Ile Gln Ile His Val Ser Ala Ser
            310             315             320

Thr Pro Pro His Leu Ser Val Gln Pro Thr Gly Leu Thr Phe Tyr Pro
            325             330             335

Ala Val Asp Val Gln Ala Phe Ala Val Leu Pro Asn Ser Ser Leu Ala
            340             345             350

Ser Leu Phe Leu Ile Gly Met His Thr Thr Gly Ser Met Glu Val Ser
    355             360             365

Ala Glu Ser Asn Arg Leu Val Gly Glu Leu Lys Leu Asp Arg Leu Leu
370             375             380             385

Leu Glu Leu Lys His Ser Asn Ile Gly Pro Phe Pro Val Glu Leu Leu
            390             395             400

Gln Asp Ile Met Asn Tyr Ile Val Pro Ile Leu Val Leu Pro Arg Val
            405             410             415

Asn Glu Lys Leu Gln Lys Gly Phe Pro Leu Pro Thr Pro Ala Arg Val
            420             425             430

Gln Leu Tyr Asn Val Val Leu Gln Pro His Gln Asn Phe Leu Leu Phe
    435             440             445

Gly Ala Asp Val Val Tyr Lys
450             455
```

METHOD OF TREATING CONDITIONS ASSOCIATED WITH INTESTINAL ISCHEMIA/REPERFUSION

This is a Continuation of U.S. application Ser. No. 08/756,164, filed Nov. 25, 1996 now U.S. Pat. No. 6,017,851, which is a Continuation of Ser. No. 08/232,527, filed Apr. 22, 1994 now U.S. Pat. No. 5,578,568.

BACKGROUND OF THE INVENTION

The present invention relates to therapeutic uses of bactericidal/permeability-increasing (BPI) protein products for the treatment of adverse physiological effects associated with intestinal ischemia/reperfusion.

Reperfusion of ischemic intestines is associated with profound cardiovascular and respiratory dysfunction that may lead to shock and death. A variety of mediators are believed to be released from the ischemic tissue that could lead to cardiorespiratory collapse, including oxygen free radicals, protanoids, and platelet activating factor.

During ischemia, breakdown of the intestinal mucosal permeability barrier may result in translocation of endotoxin and/or bacteria from the intestinal lumen. Endotoxin has been detected in the portal vein after intestinal ischemia/reperfusion. However, a role for translocated bacteria or endotoxin in intestinal ischemia/reperfusion injury has not been clearly defined.

Bactericidal/permeability-increasing protein (BPI) is a protein isolated from the granules of mammalian PMNs, which are blood cells essential in the defense against invading microorganisms. Human BPI protein has been isolated from polymorphonuclear neutrophils by acid extraction combined with either ion exchange chromatography [Elsbach, *J. Biol. Chem.*, 254:11000 (1979)] or *E. coli* affinity chromatography [Weiss, et al., *Blood*, 69:652 (1987)] referred to herein as natural BPI and has potent bactericidal activity against a broad spectrum of gram-negative bacteria. The molecular weight of human BPI is approximately 55,000 daltons (55 kD). The amino acid sequence of the entire human BPI protein, as well as the DNA encoding the protein, have been elucidated in FIG. 1 of Gray et al., *J. Biol. Chem.*, 264:9505 (1989), incorporated herein by reference.

The bactericidal effect of BPI has been shown to be highly specific to sensitive gram-negative species, while non-toxic for other microorganisms and for eukaryotic cells. The precise mechanism by which BPI kills bacteria is as yet unknown, but it is known that BPI must first attach to the surface of susceptible gram-negative bacteria. This initial binding of BPI to the bacteria involves electrostatic interactions between the basic BPI protein and the negatively charged sites on lipopolysaccharides (LPS). LPS has been referred to as "endotoxin" because of the potent inflammatory response that it stimulates. LPS induces the release of mediators by host inflammatory cells which may ultimately result in irreversible endotoxic shock. BPI binds to Lipid A, the most toxic and most biologically active component of LPS.

In susceptible bacteria, BPI binding is thought to disrupt LPS structure, leading to activation of bacterial enzymes that degrade phospholipids and peptidoglycans, altering the permeability of the cell's outer membrane, and ultimately causing cell death by an as yet unknown mechanism. BPI is also capable of neutralizing the endotoxic properties of LPS to which it binds. Because of its gram-negative bactericidal properties and its ability to neutralize LPS, BPI can be utilized for the treatment of mammals suffering from diseases caused by gram-negative bacteria, such as bacteremia or sepsis. Bahrami et al., *Int'l Endotoxin Soc. Meeting*, Vienna, Austria (August 1992), disclose the use of a BPI protein for the treatment of hemorrhagic shock.

A proteolytic fragment corresponding to the N-terminal portion of human BPI holoprotein possesses the antibacterial efficacy of the naturally-derived 55 kD human holoprotein. In contrast to the N-terminal portion, the C-terminal region of the isolated human BPI protein displays only slightly detectable anti-bacterial activity. Ooi, et al., *J. Exp. Med.*, 174:649 (1991). A BPI N-terminal fragment, comprising approximately the first 199 amino acid residues of the human BPI holoprotein and referred to as "rBPI$_{23}$", has been produced by recombinant means as a 23 kD protein. Gazzano-Santoro et al., *Infect. Immun.* 60:4754–4761 (1992).

SUMMARY OF THE INVENTION

The present invention provides novel methods for the treatment of adverse physiological effects associated with intestinal ischemia/reperfusion comprising administering BPI protein products to a subject suffering from the effects of intestinal ischemia/reperfusion. Specifically, the invention provides methods of treating the adverse physiological effects, including cardiac and hemodynamic effects, of intestinal ischemia/reperfusion resulting from a variety of causes. Such causes include mesenteric artery ischemia which is secondary to occlusions resulting from atherosclerosis, embolisms or arterial spasms; ischemia resulting from vessel occlusions in other segments of the bowel; ischemic colitis and intestinal torsion such as occurs in infants and particularly in animals. In particular, the invention provides methods for treating the adverse cardiac and other effects of intestinal ischemia and reperfusion associated with myocardial infarction.

The invention thus provides methods for treatment of sepsis-like conditions associated with intestinal ischemia/reperfusion comprising administering to a subject an amount of a BPI protein product effective to alleviate adverse physiological effects resulting from the presence of bacteria, bacterial particulates and endotoxin present in the body and in circulation in the blood.

BRIEF DESCRIPTION OF THE DRAWINGS

FIGS. 3a and 3b depict the effects of a BPI protein product on hypotension resulting from intestinal ischemia/reperfusion;

FIGS. 4a and 4b depict the effects of a BPI protein product on bradycardia resulting from intestinal ischemia/reperfusion;

FIG. 5 depicts the effects of a BPI protein product on respiratory depression resulting from intestinal ischemia/reperfusion;

FIG. 6 depicts the effects of a BPI protein product on arrythmias resulting from intestinal ischemia/reperfusion;

FIG. 7 depicts the effects of a BPI protein product on the survival time for rats subjected to intestinal ischemia/reperfusion; and FIGS. 8a and 8b depict the quantity of bacteria isolated from tissues of rats subjected to intestinal ischemia/reperfusion and the number of rats in which the bacteria were detected.

DETAILED DESCRIPTION OF THE INVENTION

Figure 1:
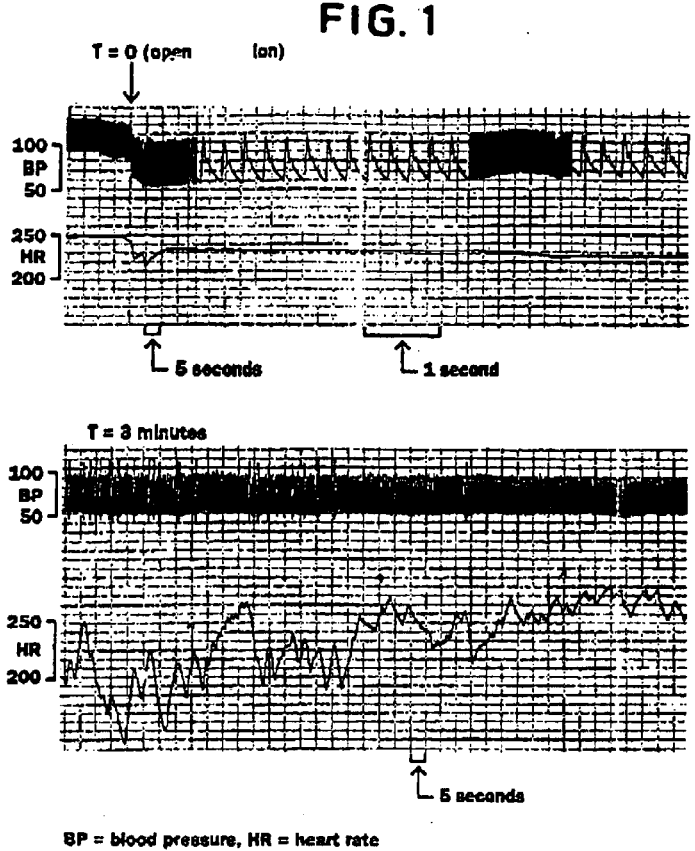
FIG. 1 depicts the hemodynamic effects of intestinal reperfusion.

The invention provides methods of treatment of the adverse effects of intestinal ischemia/reperfusion by administering BPI protein products to subjects suffering from the effects of intestinal ischemia and reperfusion. According to one aspect of the invention, the adverse cardiac and hemodynamic effects including cardiac depression, arrthymia and hypotension associated with intestinal ischemia/reperfusion are alleviated by administration of effective amounts of BPI protein products. In particular, because these studies demonstrate the adverse cardiac and hemodynamic effects of intestinal ischemia/reperfusion, the administration of BPI protein products as an adjunctive therapy for the treatment of myocardial infarction would be particularly useful. The BPI protein products are preferably administered systemically such as intravenously, or by intramuscular or subcutaneous injection.

As used herein, "BPI protein product" includes naturally and recombinantly produced bactericidal/permeability-increasing protein; natural, synthetic, and recombinant biologically active polypeptide fragments of bactericidal/permeability-increasing protein; and biologically active polypeptide analogs or variants including hybrid fusion proteins, of either bactericidal/permeability-increasing protein or biologically active fragments thereof. The BPI protein products including biologically active fragments of BPI holoprotein which are to be administered according to the methods of this invention may be generated and/or isolated by any means known in the art. U.S. Pat. No. 5,198,541, the disclosure of which is hereby incorporated by reference, discloses recombinant genes encoding and methods for expression of BPI proteins. Co-owned, copending U.S. patent application Ser. No. 07/885,501 and a continuation-in-part thereof, U.S. patent application Ser. No. 08/072,063 filed May 19, 1993, which are hereby incorporated by reference, disclose novel methods for the purification of recombinant BPI protein products expressed in and secreted from genetically transformed mammalian host cells in culture, and discloses how one may produce large quantities of recombinant BPI products suitable for incorporation into stable, homogeneous pharmaceutical preparations.

Biologically active fragments of BPI include biologically active molecules that contain the same amino acid sequence as a BPI holoprotein, except that the molecule lacks amino-terminal amino acids, internal amino acids, and/or carboxy-terminal amino acids of the holoprotein. Amino-terminal fragments of BPI comprising up to about the first 200 amino acid residues of BPI are contemplated as being particularly useful according to the invention. By way of nonlimiting examples, such fragments include those described herein and a natural 25 Kd fragment and a recombinant 23 Kd, 199 amino acid residue amino-terminal fragment of the human BPI holoprotein referred to as $rBPI_{23}$. See, Gazzano-Santoro et al., *Infect. Immun.* 60:4754–4761 (1992). In that publication, an expression vector was used as a source of DNA encoding a recombinant expression product ($rBPI_{23}$) having the 31-residue signal sequence and the first 199 amino acids of the N-terminus of the mature human BPI, as set out in SEQ ID NOS: 1 and 2 taken from Gray et al., supra, except that valine at position 151 is specified by GTG rather than GTC and residue 185 is glutamic acid (specified by GAG) rather than lysine (specified by AAG). Recombinant holoprotein referred to herein as rBPI has also been produced having the sequence set out in SEQ ID NOS: 1 and 2 taken from Gray et al., supra, with the exceptions noted for $rBPI_{23}$.

Biologically active analogs and variants of BPI include, but are not limited to, recombinant hybrid fusion proteins comprising BPI holoprotein or biologically active fragment thereof, and at least a portion of at least one other polypeptide. Such proteins are described by Theofan et al. in co-owned, copending U.S. patent application Ser. No. 07/885,911, and a continuation-in-part application thereof U.S. patent application Ser. No. 08/064,693 filed May 19, 1993, which are incorporated herein by reference in their entirety and include hybrid fusion proteins comprising, at the amino terminal end, a BPI protein or a biologically active fragment thereof and, at the carboxy terminal end, at least one constant domain of an immunoglobulin heavy chain or allelic variant thereof.

Biologically active analogs and variants of BPI also include, but are not limited to, BPI protein products wherein one or more amino acid residues have been replaced by a different amino acid. For example, co-owned, copending U.S. patent application Ser. No. 08/013,801 (Theofan et al., "Stable Bactericidal/Permeability-Increasing Protein Products and Pharmaceutical Compositions Containing the Same," filed Feb. 2, 1993) which is incorporated herein by reference, discloses polypeptide analogs of BPI and BPI fragments wherein a cysteine residue at position 132 or at position 135 is replaced by a different amino acid. A preferred BPI protein product described by this application comprises the first 199 amino acids of BPI holoprotein but wherein the cysteine at residue number 132 is substituted with alanine and is designated $rBPI_{21}\Delta cys$.

The administration of BPI protein products is preferably accomplished with a pharmaceutical composition comprising a BPI protein product and a pharmaceutically acceptable diluent, adjuvant, or carrier. The BPI protein product composition may be administered without or in conjunction with known surfactants, other chemotherapeutic agents or additional known antibiotics. A preferred pharmaceutical composition containing BPI protein products comprises BPI at a concentration of about 1 to 2 mg/ml in citrate buffered saline (0.02 M citrate, 0.15 M NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Such preferred combinations are described in co-owned, copending, U.S. patent application Ser. No. 08/190,869 filed Feb. 2, 1994 which is a continuation in part of U.S. patent application Ser. No. 08/012,360 (McGregor et al., "Improved Pharmaceutical Composition" filed Feb. 2, 1993), the disclosures of which are incorporated herein by reference.

Other BPI protein products useful according to the methods of the invention are BPI peptides such as those described in co-owned and copending U.S. patent application Ser. No. 08/209,762 filed Mar. 11, 1994 which is a continuation-in-part of U.S. patent application Ser. No. 08/183,222 filed Jan. 14, 1994 which is a continuation-in-part of U.S. patent application Ser. No. 08/093,202 filed Jul. 15, 1993 which is a continuation in part of U.S. patent application Ser. No. 08/030,644 filed Mar. 12, 1993 the disclosures of which are hereby incorporated by reference.

Practice of the methods of the present invention is illustrated in the following examples wherein: Example 1 discloses the effect of administration of a BPI protein product on blood pressure, heart rate and respiratory rate of rats subjected to intestinal ischemia/reperfusion. Example 2 discloses the effect of administration of a BPI protein product on the translocation of bacteria in rats subjected to intestinal ischemia/reperfusion.

EXAMPLE 1

A rat surgical model was used to evaluate the effects of BPI protein products on the physiological effects associated with intestinal ischemia/reperfusion. Specifically Sprague Dawley rats were anesthetized with a mixture of 80 mg/kg of ketamine and 4 mg/kg of xylazine administered by intraperitoneal injection. After a surgical plane of anesthesia was obtained, a tracheotomy was performed and a tracheal cannula was inserted. The animals breathed on their own. A catheter, made of polyethylene tubing, was placed in a femoral artery. The catheter was connected to a pressure transducer in order to measure blood pressure. Another catheter was placed in a femoral vein and connected to an infusion pump.

The abdominal contents were then exposed via a midline abdominal incision. The superior mesenteric artery (SMA) was visualized at its junction with the abdominal aorta and a silk ligature was threaded around the SMA after it had been gently loosened from the surrounding connective tissue. The loose ends of the ligature were placed outside the animal and the abdominal incision was then closed with surgical staples.

After surgery, the cardiac indices of blood pressure and heart rate were electronically recorded by measurement at the femoral artery and respiration rate was determined by visual observation for a period of about 30 to 45 minutes so that all recorded variables were stable. The ligature around the SMA was then tightened by until the SMA was occluded. The SMA remained occluded for 90 minutes at which time the ligature was loosened to allow reperfusion. Sixty minutes after the SMA was occluded 7 rats received an intravenous bolus injection of $rBPI_{21}\Delta cys$ in a vehicle comprising citrate buffered saline (0.02 M citrate, 0.15 M NaCl, pH 5.0) comprising 0.1% by weight of poloxamer 188 and 0.002% by weight of polysorbate 80 followed by a constant infusion of 2 mg/kg/hr. Seven other control rats received equal volumes of vehicle. The infusions continued until death.

Figure 2:
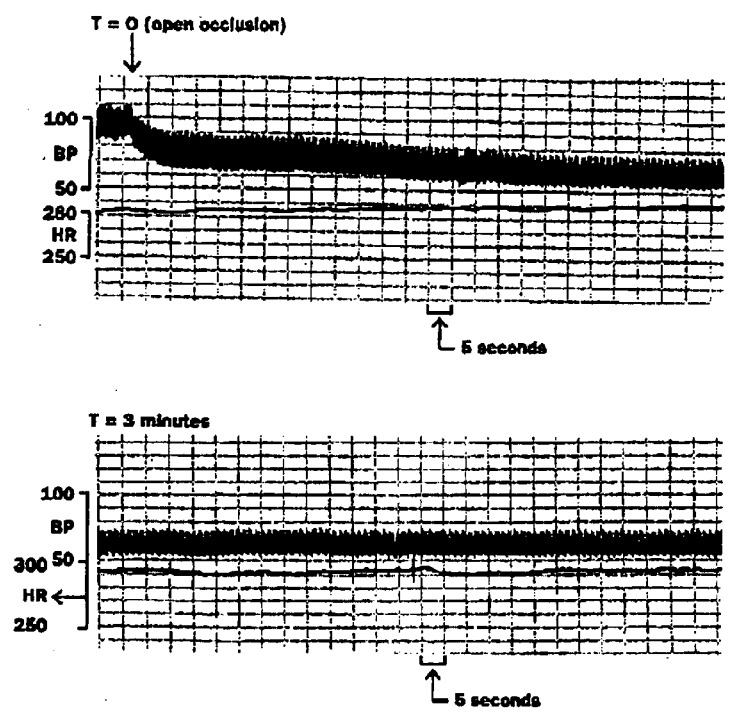
FIG. 2 depicts the effects of a BPI protein product on reperfusion-induced hemodynamic dysfunction.

Typical blood pressure and heart rate records for individual untreated and BPI treated rats are presented in FIGS. 1 and 2 respectively. Opening the SMA occlusion after 90 minutes resulted in rapid declines in blood pressure and heart rate of all rats treated with vehicle. Within a few minutes, the heart rate of all but one control rat began to oscillate, partially in phase with respiration, but also in a slower, more irregular pattern. In 5 of the 7 control rats there appeared to be missed beats which are presumably the result of arrhythmias. In contrast, irregularities of heart rate and arrhythmias were seldom observed in $rBPI_{21}\Delta cys$ treated rats. Administration of $rBPI_{21}\Delta cys$ did have an effect in reducing the hypotension resulting from intestinal ischemia/reperfusion as shown by the results in FIGS. 3a and 3b where FIG. 3a shows the results for both the ischemic and reperfusion phases of the experiment and FIG. 3b shows only the period of reperfusion. Data are shown for the first 30 minutes after opening the occlusion because all vehicle-treated rats were dead within 45 minutes and all BPI treated rats were dead within 60 minutes.

The results illustrated in FIGS. 4a and 4b (where FIG. 4a shows the results for both the ischemic and reperfusion phases of the experiment and FIG. 4b shows only the period of reperfusion) show that the administration of $rBPI_{21}\Delta cys$ had the effect of preventing bradycardia resulting from intestinal ischemia/reperfusion.

The results illustrated in FIG. 5 measuring respiratory rate show that the administration of the BPI protein product reduces respiratory depression resulting from the intestinal ischemia/reperfusion injury. The figure only presents data following reperfusion because the respiration rates for vehicle and BPI treated rats were not different prior to opening the occlusion.

The effect of intestinal ischemia and reperfusion on rats treated and untreated with the BPI protein product are set out in Table I below which illustrates the data of FIGS. 3a, 3b, 4a, 4b and 5 where t=0 is immediately before reperfusion and t=30 is after 30 minutes of reperfusion.

The results illustrated in FIG. 6 relating to arrythmia duration show that administration of the BPI protein product reduces the duration of heart rate irregularities resulting from intestinal reperfusion. For this analysis the period of time during which obvious heart rate oscillations or arrhythmias were observed was determined for each rat and then averaged. The results were statistically significant with p<0.001.

The results illustrated in FIG. 7 show that treatment with the BPI protein product increases survival time in rats suffering from intestinal ischemia/reperfusion injury (p<0.05). According to this aspect of the experiment, the time from opening the occlusion until death was recorded for each rat. In all cases death was immediately preceded by a rapid decline in respiration rate and reduction in tidal volume.

TABLE I

| | Blood Pressure (mmHg) | | Heat Rate (per min.) | | Respiratory Rate (per min.) | |
|---|---|---|---|---|---|---|
| | t = 0 | t = 30 | t = 0 | t = 30 | t = 0 | t = 30 |
| Vehicle | 96 ± 5 | 37 ± 3 | 288 ± 2 | 241 ± 16 | 51 ± 3 | 29 ± 3 |
| $rBPI_{21}\Delta cys$ | 96 ± 5 | 43 ± 5 | 284 ± 7 | 325 ± 9** | 56 ± 4 | 40 ± 4* | t = 0 is immediately before reperfusion, t = 30 is 30 minutes of reperfusion.
*p < 0.05 vs. Vehicle, **p < 0.01.

EXAMPLE 2

In an additional experiment with the rat surgical model of experiment 1 two groups of five rats each were surgically prepared and administered with either $rBPI_{21}\Delta cys$, or vehicle in the same manner and dosages as in example 1 except that a blood sample was obtained just prior to death. In addition a third group of five rats was subjected to a sham operation wherein all the surgical procedures were reproduced with the exception that the SMA was never occluded. After death, samples of tissue were obtained from the liver, spleen, and mesenteric lymph nodes. The blood was plated on trypticase soy agar and incubated overnight at 37° C. The tissue samples were then weighed and homogenized and were similarly plated and incubated overnight at 37° C. The next day the number of colonies on the plates were counted visually. The number of bacteria per gram of tissue of each organ is shown in FIG. 8a. The number of rats in which bacteria were detected is shown in FIG. 8b. These results including the sham experiment show that intestinal ischemia/reperfusion results in translocation of bacteria, most likely from the gut. Further, the results show that the administration of the BPI protein product reduced the translocation of bacteria resulting from intestinal ischemia/reperfusion. Analysis of the blood samples indicated no presence of bacteremia in any of the subject animals.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. A method of treating adverse physiological effects associated with intestinal ischemia/reperfusion wherein the adverse physiological effect is cardiac arrhythmia comprising administering to a subject suffering from the effects of intestinal ischemia/reperfusion an amount of a bactericidal/permeability-increasing (BPI) protein product effective to reduce the duration of cardiac arrhythmia resulting from intestinal ischemia/reperfusion.

2. The method of claim 1 wherein said intestinal ischemia/reperfusion is associated with occlusion of an intestinal artery.

3. The method of claim 2 wherein said intestinal ischemia/reperfusion is associated with occlusion of the mesenteric artery.

4. The method of claim 1 wherein said intestinal ischemia/reperfusion is associated with myocardial infarction.

5. The method of claim 1 wherein said intestinal ischemia/reperfusion is associated with intestinal torsion.

6. The method of claim 1 wherein the BPI protein product is an amino-terminal fragment of BPI.

7. The method of claim 1 wherein the BPI protein product is rBPI$_{21}$Δcys.

8. The method of claim 1 wherein the BPI protein product is administered in conjunction with a pharmaceutically-acceptable diluent, adjuvant or carrier.

* * * * *